(12) United States Patent
Keller

(10) Patent No.: US 7,160,303 B2
(45) Date of Patent: Jan. 9, 2007

(54) MEDICAL IMPLANT WITH A SECURED BONE SCREW

(75) Inventor: Arnold Keller, Kayhude (DE)

(73) Assignee: Cervitech, Inc., Rockaway, NJ (US)

( * ) Notice: Subject to any disclaimer, the term of this patent is extended or adjusted under 35 U.S.C. 154(b) by 59 days.

(21) Appl. No.: 10/349,175

(22) Filed: Jan. 23, 2003

(65) Prior Publication Data

US 2005/0090826 A1 Apr. 28, 2005

(51) Int. Cl.
*A61B 17/56* (2006.01)
*A61F 2/30* (2006.01)

(52) U.S. Cl. .................................................. 606/70

(58) Field of Classification Search ................ 606/53, 606/60, 69, 70, 71, 72, 73; 411/114, 115, 411/187–189; 433/174, 173, 175, 176, 201.1
See application file for complete search history.

(56) References Cited

U.S. PATENT DOCUMENTS

| | | | | |
|---|---|---|---|---|
| 2,229,892 A | * | 1/1941 | Hosking | 411/187 |
| 3,342,236 A | * | 9/1967 | Clark | 411/189 |
| 4,872,839 A | * | 10/1989 | Brajnovic | 433/173 |
| 5,100,405 A | * | 3/1992 | McLaren | 606/72 |
| 5,362,235 A | * | 11/1994 | Daftary | 433/172 |
| 5,433,606 A | * | 7/1995 | Niznick et al. | 433/173 |
| 5,514,138 A | * | 5/1996 | McCarthy | 606/65 |
| 5,709,686 A | * | 1/1998 | Talos et al. | 606/69 |
| 5,968,047 A | * | 10/1999 | Reed | 606/76 |
| 6,030,389 A | * | 2/2000 | Wagner et al. | 606/71 |
| 6,227,782 B1 | * | 5/2001 | Bowling et al. | 411/114 |
| 6,238,132 B1 | * | 5/2001 | Plantan et al. | 403/343 |
| 6,331,179 B1 | * | 12/2001 | Freid et al. | 606/61 |
| 6,394,725 B1 | * | 5/2002 | Dicke | 411/399 |
| 6,497,573 B1 | * | 12/2002 | Wagner et al. | 433/173 |
| 6,730,091 B1 | * | 5/2004 | Pfefferle et al. | 606/70 |
| 2004/0076924 A1 | * | 4/2004 | Kim | 433/173 |

\* cited by examiner

*Primary Examiner*—Eduardo C. Robert
*Assistant Examiner*—Anuradha Ramana
(74) *Attorney, Agent, or Firm*—Morrison & Foerster LLP

(57) ABSTRACT

A medical implant has a secured bone screw which is guided through a bore of the implant. The bore has a thread matching the thread of the bone screw. Between the head of the bone screw and the thread thereon, there is an unthreaded portion whose diameter is not greater than the free inside diameter of the threaded bore. These threads prevent axial passage of the bone screw through the bore without turning. Turning is inhibited or excluded by an arrangement preventing turning.

5 Claims, 1 Drawing Sheet

MEDICAL IMPLANT WITH A SECURED BONE SCREW

FIELD AND BACKGROUND OF THE INVENTION

With medical implants which are to be fastened to bone using a bone screw, it is often necessary to prevent backward migration of the screw from its assigned position, so that it cannot pose a danger to adjacent organs. It is not enough, as is known in the prior art, to secure the screws against turning in the direction of unscrewing, because, if their thread turns are engaged loosely in the bone substance, there is a danger of their moving back axially without any appreciable turning. It is therefore known to secure the screws by providing the implant with covering arrangements which, after the screw has been screwed in, are placed over the screw head in order to prohibit its backward movement. Such covering arrangements, however, take up additional space, which can sometimes be undesirable.

SUMMARY OF THE INVENTION

The invention therefore aims to provide a means of securing bone screws without the need to cover the screw head.

The solution according to the invention lies in the features of the invention as disclosed in this application. Accordingly, the invention provides that the bone screw is guided through a bore of the implant, which bore is provided with a thread matching the thread of the screw, that the screw shank between the screw head and the thread has an unthreaded portion whose length is at least as great as the length of the threaded bores, and that the implant and the screw act together to inhibit reverse turning of the screw. When the screw is located in its assigned position, the unthreaded portion of the screw shank lies in the threaded bore of the implant. The threads of the bore and of the screw do not engage in one another in this state. The securing of the screw against backward movement is achieved by the fact that the screw thread cannot pass axially through the threaded bore. The mutually adjoining, final turns of the bore thread and of the screw thread form axial abutments which prevent backward movement of the screw. Escape of the screw from the implant would then only be possible if the screw thread were able to move by turning into the thread of the bore. This, however, is prevented by the barrier against backward turning.

BRIEF DESCRIPTION OF THE DRAWINGS

The invention is explained in more detail below with reference to the drawings which depicts an advantageous illustrative embodiment. In the drawings.

DETAILED DESCRIPTION OF THE INVENTION

Figure 1:
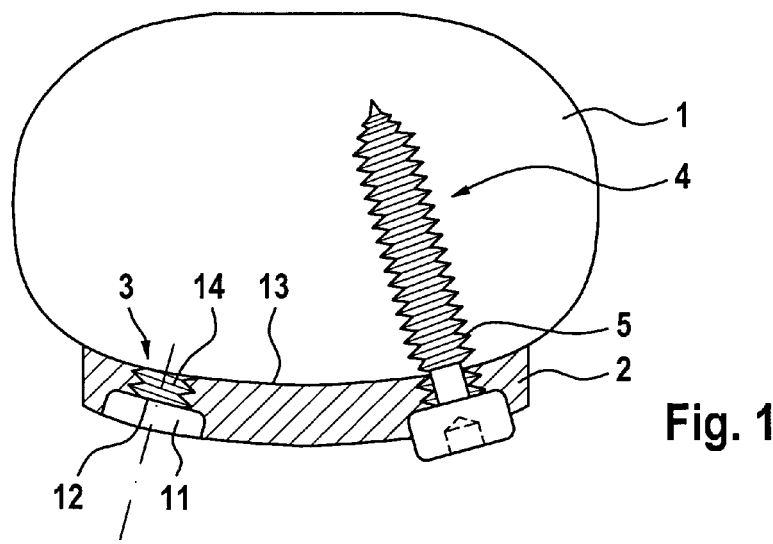
FIG. 1 shows a cross section through an endoprosthesis along line I—I in FIG. 2.
Figure 4:
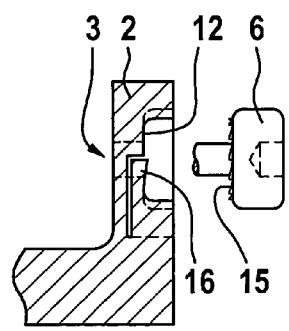
FIG. 4 shows a cross section through the bone screw used in the arrangement, looking toward the shank-side face of the screw head.
Figure 2:
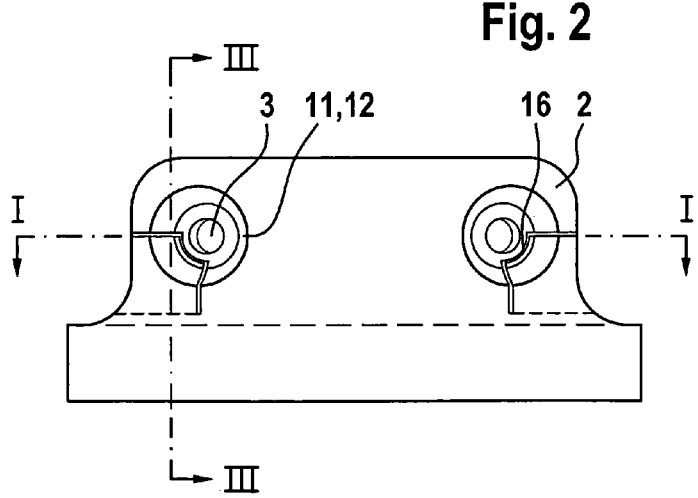
FIG. 2 shows a ventral view of the prosthesis.

An endoprosthesis is shown, with a plate 1 on the edge of which a flange 2 is arranged, said flange having two bores 3 which are intended to receive bone screws 4, which in turn are intended to fasten the flange 2 on the surface of a bone. For anchoring in the bone, the bone screws have a thread 5 which, in the portion near the tip of the screw seen on the right in FIG. 1, is only indicated by broken lines. At the other end, the shank of the screw 4 is provided with a head 6 which has surfaces for engagement of a screwing instrument, which surfaces, in the example shown, are designed as a hexagon socket 7. An unthreaded portion 10 is situated between the shank-side face 8 of the screw head 6 and the adjacent end 9 of the thread 5.

The associated bore 3 can (but does not need to) have a seat 11 for completely or partially receiving the screw head 6, said seat 11 forming a face 12 for supporting the rear face 8 of the screw head 6. The bore portion between the face 12 and the rear face 13 of the flange 2 of the bore comprises a thread 14 which matches the thread 5 of the screw 4. The length of the threaded portion of the bore between the faces 12 and 13 is not greater than the axial length of the unthreaded portion 10 of the screw and not much shorter. The diameter of the unthreaded portion 10 of the screws is not greater than the free core cross section in the bore 3. Accordingly, after the screw 4 has been fully screwed in, the screw thread 5 is free from the thread 14 of the bore 3. The screw can thus be turned freely, as is necessary in order to draw the flange 2 fully onto the surface of the bone by tightening the screw in the bone.

Figure 3:
FIG. 3 shows a cross section along line III—III in FIG. 2.

The rear end 9 of the screw thread 5 and the adjoining end of the thread 14 in the bore 3 form abutments which prohibit an axial, non-rotational backward movement of the screw 4 onto the flange 2 of the implant. To ensure that backward turning is also prevented, the screw and the implant are provided with an arrangement preventing turning. This arrangement can be of any very simple kind known generally in the prior art for preventing backward turning of screws. For example, the screw head can be provided with serrations 15 on its shank-side face in order to interact with corresponding members of the flange 2 and thereby prevent backward turning. In the present example, the members preventing backward turning in FIG. 3 are indicated in the form of a spring tongue 16 which protrudes resiliently from the base face 12 of the seat 11 of the flange, so that its edge can come into engagement with the serrations 15. The arrangement is configured in such a way that the screw can be turned only in the direction in which it is screwed into the bone. If an attempt is made to turn it in the direction of unscrewing, the end edge of the spring 16 comes into engagement with the teeth 15 and prevents further backward turning.

The thread 14 in the bore 3 does not have to be particularly long. On the contrary, it can be extremely short. There does not even have to be a complete thread turn. It is enough, for example, to provide the suggestion of a thread turn in the form of a projection on one side of the bore, said projection being just large enough to prevent the axial passage of the threaded part of the screw.

The invention claimed is:

1. A medical implant with a secured bone screw for implantation in and engagement with a bone, comprising:
   an implant body having a threaded bore formed therethrough, the threaded bore having a free inside diameter between corresponding thread tips; a bone screw having threads formed thereon configured to engage with the bone and hold the implant in engagement with the bone when the implant is implanted and having a head, the bone screw being configured to be guided through the bore; and an arrangement provided for the bone screw for preventing backward turning of the bone screw within the implant and turning of the bone screw out of the implant after the implant is in engagement with the bone, wherein the bone screw has a threaded portion having threads that match the threaded bore and an unthreaded portion between the head and the threaded portion having an outer diameter that is not greater than the free inside diameter of the threaded bore;

wherein the bone screw has a length such that when the bone screw is fully screwed into the implant body, its tip projects beyond a surface of the implant body opposite a surface of the implant body into which the bone screw enters the threaded bore; and wherein the unthreaded portion of the bone screw is at least as long as the threaded bore.

2. The medical implant of claim 1, wherein the medical implant further comprises axial abutments between mutually adjoining, final turns of the bore thread and the bone screw thread.

3. The medical implant of claim 1, wherein the arrangement for preventing backward turning of the bone screw is configured to engage the bone screw when the threaded portion of the bone screw becomes clear of the threaded bore when screwing the bone screw through the implant into the bone to bring the implant into engagement with the bone.

4. The medical implant of claim 1, wherein the bone screw is pointed for engagement with the bone.

5. The medical implant of claim 1, wherein the arrangement for preventing backward turning of the bone screw comprises a tongue on the face of the implant adjacent the opening of the threaded bore and corresponding projections on a shank-side face of a head of the bone screw.

* * * * *

UNITED STATES PATENT AND TRADEMARK OFFICE
CERTIFICATE OF CORRECTION

PATENT NO.        : 7,160,303 B2
APPLICATION NO.   : 10/349175
DATED             : January 9, 2007
INVENTOR(S)       : Arnold Keller It is certified that error appears in the above-identified patent and that said Letters Patent is hereby corrected as shown below:

In Column 2, Line 54, there is a misprint. Line 54 should read -- being just large enough to prevent the axial passage of the --.

In Column 2, Line 55, there is a misprint. Line 55 should read -- threaded part of the screw.--

Signed and Sealed this

Tenth Day of April, 2007

JON W. DUDAS
*Director of the United States Patent and Trademark Office*